United States Patent [19]

Dwyer et al.

[11] Patent Number: 5,336,478
[45] Date of Patent: * Aug. 9, 1994

[54] HIGHLY SILICEOUS POROUS CRYSTALLINE MATERIAL

[75] Inventors: Francis G. Dwyer, West Chester; Ernest W. Valyocsik, Yardley, both of Pa.

[73] Assignee: Mobil Oil Corp., Fairfax, Va.

[*] Notice: The portion of the term of this patent subsequent to Feb. 20, 2007 has been disclaimed.

[21] Appl. No.: 101,791

[22] Filed: Aug. 2, 1993

Related U.S. Application Data

[63] Continuation of Ser. No. 695,609, Jan. 28, 1985, abandoned, which is a continuation-in-part of Ser. No. 373,451, Apr. 30, 1982, abandoned, which is a continuation-in-part of Ser. No. 629,743, Jul. 10, 1984, Pat. No. 4,902,406, which is a continuation of Ser. No. 373,452, Apr. 30, 1982, abandoned.

[51] Int. Cl.$^5$ .............................................. C01B 33/34
[52] U.S. Cl. ..................................................... 423/708
[58] Field of Search ......................................... 423/328

[56] References Cited

U.S. PATENT DOCUMENTS

| | | | |
|---|---|---|---|
| 4,481,177 | 11/1984 | Valyocsik | 423/329 |
| 4,556,477 | 12/1985 | Dwyer | 208/111 |
| 4,574,043 | 3/1986 | Chester et al. | 208/111 |
| 4,605,488 | 8/1986 | Chester et al. | 208/111 |
| 4,717,465 | 1/1988 | Chen et al. | 208/59 |
| 4,783,555 | 11/1988 | Atkins | 502/77 |
| 4,810,357 | 3/1989 | Chester et al. | 208/97 |
| 4,814,543 | 3/1989 | Chen et al. | 585/739 |
| 4,902,406 | 2/1990 | Valyocsik | 208/118 |
| 4,919,788 | 4/1990 | Chen et al. | 208/49 |
| 5,063,038 | 11/1991 | Kirker et al. | 502/77 |
| 5,135,638 | 8/1992 | Miller | 585/739 |
| 5,137,194 | 10/1992 | Rahmim et al. | 585/671 |
| 5,810,357 | 3/1989 | Chester et al. | 208/97 |

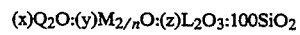

*Primary Examiner*—Asok Pal
*Attorney, Agent, or Firm*—Alexander J. McKillop; Dennis P. Santini; Edward F. Kenehan, Jr.

[57] ABSTRACT

A new zeolite, designated ZSM-22, is disclosed and claimed. The new zeolite has the composition, in the anhydrous state, expressed in terms of mole ratios of oxides as follows:

$$(x)Q_2O:(y)M_{2/n}O:(z)L_2O_3:100SiO_2$$

wherein $Q_2O$ is the oxide form of an organic compound, M is an alkali or alkaline earth metal having a valence n, e.g., Na, K, Cs or Li and wherein $x=0-2.0$, $y=0-2.0$, $z=0-5$, and $L=Al$. Also disclosed are methods of preparing ZSM-22, e.g., with an alkane diamine directing agent, and uses of ZSM-22 as catalysts, e.g., in hydrocarbon conversion reactions.

12 Claims, No Drawings

HIGHLY SILICEOUS POROUS CRYSTALLINE MATERIAL

CROSS-REFERENCE TO RELATED APPLICATIONS

This application is a continuation of U.S. application Ser. No. 06/695,609, filed Jan. 28, 1985, now abandoned, which is a continuation-in-part of copending U.S. application Ser. No. 373,451, filed Apr. 30, 1982, now abandoned, in the name of Francis G. Dwyer.

Ser. No. 06/695,609 is also a continuation-in-part of copending U.S. application Ser. No. 629,743, filed Jul. 10, 1984, now U.S. Pat. No. 4,902,406, in the name of Ernest W. Valyocsik, which is a continuation of U.S. application Ser. No. 373,452, filed Apr. 30, 1982, now abandoned, in the name of Ernest W. Valyocsik.

This application is also related to copending U.S. application Ser. No. 373,453, filed Apr. 30, 1982, in the name of L. Brewster Young, now U.S. Pat. No. 5,248,841.

Ser. No. 06/695,609 is also related to U.S. application Ser. No. 668,244, filed Nov. 5, 1984, now abandoned in the name of Ernest W. Valyocsik, which is a continuation of U.S. application Ser. No. 448,133, filed Dec. 9, 1982, in the name of Ernest W. Valyocsik. This Ser. No. 448,133 is now U.S. Pat. No. 4,481,177.

Ser. No. 06/695,609 is also related to copending U.S. application Ser. No. 652,164, filed Sep. 19, 1984, now U.S. Pat. No. 5,254,770, which is a continuation of U.S. application Ser. No. 531,585, filed Sep. 13, 1983, now abandoned, which is a continuation of U.S. application Ser. No. 413,958, filed Sep. 1, 1982, now abandoned all of the applications in this chain being in the name of David H. Olson, Ernest W. Valyocsik and R. Bruce Calvert.

The entire disclosures of these above-referenced applications and U.S. patent are expressly incorporated herein by reference.

1. Field of the Invention

This invention relates to a novel siliceous porous crystalline material designated ZSM-22.

This invention also relates to methods of synthesizing ZSM-22. This invention also relates to the use of ZSM-22 as a catalyst.

2. Description of Related Art

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties.

Such molecular sieves, both natural and synthetic, include a wide variety of positive ion-containing crystalline aluminosilicates. These aluminosilicates can be described as having a rigid three-dimensional framework of $SiO_4$ and $AlO_4$ in which the tetrahedra are cross-linked by the sharing of oxygen atoms whereby the ratio of the total aluminum and silicon atoms to oxygen atoms is 1:2. The electrovalence of the tetrahedra containing aluminum is balanced by the inclusion in the crystal of a cation, for example an alkali metal or an alkaline earth metal cation. This can be expressed by the relationship of aluminum to the cations, wherein the ratio of aluminum to the number of various cations, such as Ca/2, Sr/2, Na, K, Cs or Li, is equal to unity. One type of cation may be exchanged either entirely or partially with another type of cation utilizing ion exchange techniques in a conventional manner. By means of such cation exchange, it has been possible to vary the properties of a given aluminosilicate by suitable selection of the cation. The spaces between the tetrahedra are occupied by molecules of water prior to dehydration.

Prior art techniques have resulted in the formation of a great variety of synthetic aluminosilicates. The aluminosilicates have come to be designated by letter or other convenient symbols, as illustrated by zeolite A (U.S. Pat. No. 2,882,243), zeolite X (U.S. Pat. No. 2,882,244), zeolite Y (U.S. Pat. No. 3,130,007), zeolite ZK-5 (U.S. Pat. No. 3,247,195), zeolite ZK-4 (U.S. Pat. No. 3,314,752), zeolite ZSM-5 U.S. Pat. No. 3,702,886), zeolite ZSM-11 (U.S. Pat. No. 3,709,979), zeolite ZSM-12 (U.S. Pat. No. 3,832,449), zeolite ZSM-20 (U.S. Pat. No. 3,972,983), ZSM-35 (U.S. Pat. No. 4,016,245), zeolites ZSM-21 and ZSM-38 (U.S. Pat. No. 4,046,859), and zeolite ZSM-23 (U.S. Pat. No. 4,076,842).

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5, up to infinity. U.S. Pat. No. 3,941,871, now U.S. Pat. No. Re. 29,948, the entire contents of which are incorporated herein by reference, discloses a porous crystalline silicate zeolite made from a reaction mixture containing no deliberately added alumina in the recipe and exhibiting the X-ray diffraction pattern characteristic of ZSM-5 type zeolites. U.S. Pat. Nos. 4,061,724, 4,073,865 and 4,104,294, the entire contents of all three patents being incorporated herein by reference, describe crystalline silica compositions of varying alumina and metal content.

SUMMARY OF THE INVENTION

The present invention is directed to a novel highly siliceous porous crystalline material. The crystalline material of this invention has been designated as the zeolite ZSM-22 and it has a characteristic X-ray diffraction pattern, as set forth in Table 1, discussed below.

The highly siliceous material of this invention comprises crystalline, three-dimensional continuous framework silicon-containing structures or crystals which result when all the oxygen atoms in the tetrahedra are mutually shared between tetrahedral atoms of silicon or aluminum, and which can exist with a network of mostly $SiO_2$, i.e., exclusive of any intracrystalline cations. Similar structures form building blocks of materials such as quartz, cristobalite and a long list of zeolite structures such as ZSM-5, ZSM-11, ZSM-12, ZSM-23, ZSM-35, ZSM-38, ZSM-48, mordenite and perhaps even faujasite. Not all zeolite structures are known to exist at this time in predominantly $SiO_2$—containing compositions—so the above class of materials does not presently include zeolites such as zeolite A.

The zeolite of the present invention also contains a relatively minor amount of $Al_2O_3$ and can produce a product with a $SiO_2$ to $Al_2O_3$ mole ratio of about 20 to about ∞. In the as-synthesized form, the ZSM-22 may have a calculated composition, in terms of moles of oxides, after dehydration, per 100 moles of silica, as follows:

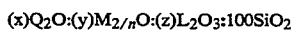

wherein $Q_2O$ is the oxide form of an organic compound containing an element of Group 5-B (as defined in the Table of the Elements-National Bureau of Standards, Fischer Scientific Co. Catalog No. 5-702-10), e.g., N or P, preferably N, containing at least one alkyl or aryl group having at least 2 carbon atoms, M is an alkali metal or an alkaline earth metal having a valence n, and wherein x=0.01-2.0, y=0-2.0, z=0-5, and L=Al.

ZSM-22 can further be identified by its sorptive characteristics and its X-ray diffraction pattern. The original cations of the as-synthesized ZSM-22 may be replaced at least in part by other ions using conventional ion exchange techniques. It may be necessary to precalcine the ZSM-22 zeolite crystals prior to ion exchange. The replacing ions introduced to replace the original alkali, alkaline earth and/or organic cations may be any that are desired so long as they can pass through the channels within the zeolite crystals. Desired replacing ions are those of hydrogen, rare earth metals, metals of Groups IB, IIA, IIB, IIIA, IIIB, IVA, IVB, VIB and VIII of the Periodic Table. Among the metals, those particularly preferred are rare earth metals, manganese, zinc and those of Group VIII of the Periodic Table.

ZSM-22 zeolite described and claimed herein has a definite X-ray diffraction pattern, set forth below in Table I, which distinguishes it from other crystalline materials.

TABLE I

Most Significant Lines of ZSM-22

| Interplanar d-spacings (Å) | Relative Intensity (I/Io) |
| --- | --- |
| 10.9 ± 0.2 | M-VS |
| 8.7 ± 0.16 | W |
| 6.94 ± 0.10 | W-M |
| 5.40 ± 0.08 | W |
| 4.58 ± 0.07 | W |
| 4.36 ± 0.07 | VS |
| 3.68 ± 0.05 | VS |
| 3.62 ± 0.05 | S-VS |
| 3.47 ± 0.04 | M-S |
| 3.30 ± 0.04 | W |
| 2.74 ± 0.02 | W |
| 2.52 ± 0.02 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the spectrometer. From these, the relative intensities, 100 $I/I_o$, where $I_o$ is the intensity of the strongest line or peak, and d (obs.) the interplanar spacing in Å, corresponding to the recorded lines, were determined. In Table I, the relative intensities are given in terms of the symbols vs=very strong, s=strong, m=medium, w=weak, etc. It should be understood that this X-ray diffraction pattern is characteristic of all the species of ZSM-22 zeolite compositions. Ion exchange of the alkali metal cations with other ions results in a zeolite which reveals substantially the same X-ray diffraction pattern with some minor shifts in interplanar spacing and variation in relative intensity. Other minor variations can occur, depending on the silica to alumina ratio of the particular sample, as well as its degree of thermal treatment.

The present invention is also directed to a process for manufacturing the zeolite ZSM-22.

The ZSM-22 highly siliceous zeolite can be suitably prepared from a reaction mixture containing a source of silica, an alkane diamine, an alkali metal oxide or an alkaline earth metal oxide, e.g., sodium, potassium, cesium, calcium or strontium, water, and alumina, and having a composition, in terms of mole ratios of oxides, falling within the following ratios:

| Reactants | | Broad | Preferred |
| --- | --- | --- | --- |
| $SiO_2/Al_2O_3$ | = | 20 to | 30 to 1000 |
| $H_2O/SiO_2$ | = | 10 to 100 | 20 to 60 |
| $OH^-/SiO_2$ | = | 0 to 0.3 | 0.1 to 0.2 |
| $M^+/SiO_2$ | = | 0 to 2.0 | 0.1 to 1.0 |
| $RN/SiO_2$ | = | 0.01 to 2.0 | 0.05 to 1.0 | wherein RN is a $C_2$-$C_{12}$ alkane diamine of the formula $H_2N$—$(CH_2)_n$—$NH_2$ (abbreviated $C_nDN$), n=2 to 12, and preferably is 5 to 8, and M is an alkali metal or an alkaline earth metal and maintaining the mixture at crystallization temperature until crystals of the ZSM-22 zeolite are formed. Thereafter, the crystals are separated from the liquid by any conventional means, washed and recovered. The ZSM-22 zeolite can be used in aromatics alkylation reactions (e.g., toluene alkylation by methanol and ethylene), toluene disproportionation, selective cracking of a meta/para-cymene mixture, and conversion of various oxygenates to gasoline-grade hydrocarbons.

DETAILED DESCRIPTION OF THE INVENTION

The zeolite of this invention freely sorbs normal hexane and has a pore dimension greater than about 4 Angstroms. In addition, the structure of the zeolite must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous hydrocarbon conversions, although puckered structures exist such as TMA offretite which is a known effective zeolite. Also, such twelve-membered structures can be conceived that may be operative due to pore blockage or other causes.

Rather than attempt to judge from crystal structure whether or not a zeolite possesses the necessary constrained access, a simple determination of the "constraint index" may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. (288° C.) and 950° F. (510° C.) to give an overall conversion between 10% and 60%. The mixture of hydrocarbons is passed at a 1 liquid hourly space velocity (LHSV), i.e., 1 volume of liquid hydrocarbon per volume of zeolite per hour over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} (\text{fraction of n-hexane remaining})}{\log_{10} (\text{fraction of 3-methylpentane remaining})}$$

The constraint index approximates the ratio of the cracking rate constants for the two hydrocarbons. Zeolites of the present invention are those having a constraint index in the approximate range of 1 to 12, preferably 1 to 5, and most preferably about 2.5 to about 3.0. Constraint Index (CI) values for some typical zeolites are:

| Zeolite | C.I. |
| --- | --- |
| ZSM-5 | 8.3 |
| ZSM-11 | 8.7 |
| ZSM-12 | 2 |
| ZSM-23 | 9.1 |
| ZSM-38 | 2 |
| ZSM-35 | 4.5 |
| Clinoptilolite | 3.4 |
| IMA Offretite | 3.7 |
| Beta | 1.5 |
| ZSM-4 | 0.5 |
| H-Zeolon | 0.4 |
| REY | 0.4 |
| Amorphous Silica-Alumina (non-zeolite) | 0.6 |
| Erionite | 38 |

It is to be realized that the above constraint index values typically characterize the specified zeolites but that these are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possible occluded contaminants and binders intimately combined with the zeolite, may affect the constraint index. It will accordingly be understood by those skilled in the art that the constraint index, as utilized herein, while affording a highly useful means for characterizing the zeolites of interest is approximate, taking into consideration the manner of its determination; with probability, in some instances, of compounding variable extremes.

While the above experimental procedure will enable one to achieve the desired overall conversion of 10 to 60% for most catalyst samples and represents preferred conditions, it may occasionally be necessary to use somewhat more severe conditions for samples of very low activity, such as those having a very high silica to alumina mole ratio. In those instances, a temperature of up to about 1000° F. and a liquid hourly space velocity of less than one, such as 0.1 or less, can be employed in order to achieve a minimum total conversion of about 10%.

The new ZSM-22 highly siliceous zeolite can be suitably prepared from a reaction mixture containing a source of silica, $Q_2O$, an alkali metal oxide, e.g., sodium, potassium or cesium, water, and alumina, wherein $Q_2O$ is the oxide form of an organic compound, and maintaining the mixture at crystallization temperature until crystals of the new ZSM-22 zeolite are formed. Thereafter, the crystals are separated from the liquid by any conventional means, washed and recovered.

Crystallization can be carried out at either static or stirred conditions in a reactor vessel, e.g., a polypropylene jar, teflon lined or stainless steel autoclaves, at 80° C. (176° F.) to about 210° C. (410° F.) for about 6 hours to 150 days. Thereafter, the crystals are separated from the liquid and recovered. The composition can be prepared utilizing materials which supply the appropriate oxide. Such materials include aluminates, alumina, silicates, sodium silicate, silica hydrosol, silica gel, silicic acid, sodium, potassium or cesium hydroxide, and an alkane diamine. Suitable diamines are, e.g., ethanediamine, propanediamine, butanediamine, pentanediamine, hexanediamine, heptanediamine, octanediamine, nonanediamine, decanediamine, undecanediamine, duodecanediamine. The reaction mixture can be prepared either batchwise or continuously. Crystal size and crystallization time of the new crystalline material will vary with the nature of the reaction mixture employed and the crystallization conditions.

As set forth above, the ZSM-22 zeolite can be prepared with an alkane diamine directing agent at a relatively wide range of $SiO_2/Al_2O_3$ ratios of about 20 to about infinity ($\infty$). However, it has been found that larger alkali metal cations, e.g., $K^+$ and $Cs^+$, are preferably used with an alkane diamine directing agent at the $SiO_2/Al_2O_3$ ratios of about 20 to about 90 to obtain ZSM-22 crystals substantially free of impurities or other zeolites. The potassium ($K^+$) cation is preferred at such low $SiO_2/Al_2O_3$ ratios because cesium (Cs) appears to decrease the reaction rate. At the $SiO_2/Al_2O_3$ ratios of 90 or above and using an alkane diamine directing agent, smaller cations, e.g., sodium ($Na^+$) cations, are preferably used to produce substantially 100% crystalline ZSM-22.

In an as-synthesized form, ZSM-22 may have a calculated composition, in terms of moles of oxides, after dehydration, per 100 moles of silica, as follows:

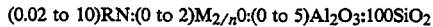

$$(0.02 \text{ to } 10)RN:(0 \text{ to } 2)M_{2/n}0:(0 \text{ to } 5)Al_2O_3:100SiO_2$$

wherein RN is a $C_2$-$C_{12}$ alkane diamine and M is an alkali metal or an alkaline earth metal having a valence n, e.g., Na, K, Cs, Li, Ca or Sr.

Preliminary data indicates that the ZSM-22 zeolite has an orthorhombic noncentral structure consisting substantially of 5 and 6-member rings which form a substantially unidirectional 10-ring channel system. Four member rings appear to be completely absent from the structure, which may explain, at least to some extent, the relatively high thermal stability of ZSM-22. (A sample of ZSM-22 was found to be thermally stable after heating at 550° C. in air for 20 hours, and substantially steam stable, after the treatment at 920° F.–about 493° C.—for 5 hours in 1 atm saturated steam). The ZSM-22 crystalline structure appears to be similar to zeolites of the ZSM-5 family, particularly ZSM-5, ZSM-11, ZSM-23, and ZSM-35. Accordingly, its performance characteristic may be similar to those of the aforementioned zeolites of the ZSM-5 family. Preliminary data, however, does not completely support this hypothesis. For example, the $\alpha$ activity, set forth in Table II, of ZSM-22 samples is less than that predicted for the ZSM-5 zeolite of equivalent $SiO_2/Al_2O_3$ ratios. Without wishing to be bound by any theory of operability, it is possible that trace amounts of the potassium cation ($K^+$) strategically located within the unidimensional channels may account for the reduced activity of the zeolite. Extractions of ZSM-22 samples with hydrochloric acid (HCl) to reduce the $K^+$ level in the zeolite may be effective in improving $\alpha$ activity.

TABLE II

Comparison of Activities for ZSM-22 and ZSM-5

| Form | Wt % K present | $\delta$-value Observed | (expected) |
|---|---|---|---|
| As-synthesized | 2.3 | — | (—) |
| TMA-exchanged[a] | 0.41 | 35 | ($\delta$ = 130)[c] |
| NH$_4$-exchanged[b] | 0.04 | 61 | ($\delta$ = 130)[c] |

[a]98° C., stirred 6 hrs. in 0.5 $\underline{N}$ tetramethyl ammonium bromide (TMABr).
[b]98° C., stirred 6 hrs. in 1.0 $\underline{N}$ NH$_4$NO$_3$.
[c]$\delta$-value expected for ZSM-5 of equivalent $SiO_2/Al_2O_3$ ratio.

The alpha-test ($\alpha$-test) is an indication of the relative catalytic cracking activity of the catalyst compared to a standard catalyst. The value of $\alpha$ is the relative rate constant (rate of n-hexane conversion per unit volume of catalyst per unit time). It is based on the activity of highly active silica-alumina cracking catalyst taken as $\alpha = 1$.

The $\alpha$-test is further described in a letter to the editor, entitled "Superactive Crystalline Alumino-Silicate Hydrocarbon Cracking Catalysts", by P. B. Weisz and J. N. Miale, *Journal of Catalysis*, Vol. 4, pp. 527–529 (August 1965) and in U.S. Pat. No. 3,354,078, the entire contents of both of which are incorporated herein by reference.

The sorption of hydrocarbons by ZSM-22 has also been surveyed and the results are summarized in Table III. Sorption capacities for n-hexane (normal hexane), cyclohexane, and water are about 4% by weight, or about one third that of ZSM-5. Without wishing to be bound by any theory of operability, it is thought that the reduced sorption capacity may be due to the unidimensional channel system of ZSM-22, but residual $K^+$ within the channels may also contribute to the relatively low sorption capacities. Cyclohexane and o-xylene sorption is relatively slow, making it difficult to determine equilibrium capacities.

TABLE III

ZSM-22 Sorption Data

| Sample | Form | Sorptions (wt %)[a] | | | | |
|---|---|---|---|---|---|---|
| | | n-hexane | 3-methyl-pentane | Cyclohexane[c] | H$_2$O | o-xylene[b] |
| 1 | Hydrogen (H) | 3.9 | — | 2.8 | — | — |
| 2 | H | 4.2 | 3.9 | 1.1 | — | ~2 |
| 3 | H | 4.1 | — | 3.3 | 4.7 | — |
| 4 | as-synthesized | 3.4 | — | — | — | — |

[a]Hydrocarbons: pressure = 20 mm, temperature = 25° C.; water-pressure = 12 mm, temperature = 25° C.
[b]pressure = 3.7 mm, temperature = 120° C.
[c]slow tailing sorption, nonequilibrium values.

The ZSM-22 zeolite, as synthesized with alkane diamine directing agents, tends to crystallize as agglomerates of elongated crystals having the size of about 0.5 to about 2.0 microns ($\mu$). Ballmilling fractures these crystals into smaller size crystallites (about 0.1 $\mu$) without significant loss of crystallinity. The zeolite can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

While synthetic ZSM-22 zeolites may be used in a wide variety of hydrocarbon conversion reactions, they are notably useful in the processes of polymerization, aromatization and cracking. Other hydrocarbon conversion processes for which ZSM-22 may be utilized in one or more of its active forms include, for example, hydrocracking and converting light aliphatics to aromatics, e.g., as disclosed in U.S. Pat. No. 3,760,024, the entire contents of which are incorporated herein by reference. ZSM-22 is para-selective in certain of its catalytic reactions.

Employing a catalytically active form of the ZSM-22 catalyst for polymerization of olefins containing liquid or gaseous charge stocks, such charge stocks can be polymerized at temperatures between 290° and 450° C. (about 550° and 850° F.) at an hourly space velocity of between 0.5 and 50 WHSV (weight hourly space velocity) and a pressure of between 0.1 and 800 psig. In employing the catalyst of the present invention for aromatization of gaseous of liquid charge stocks which may be olefinic or paraffinic, with or without aromatics present, such stocks can be aromatized at temperatures of between 430° and 650° C. (about 800° and 1200° F.), pressures of 1 to 10 atmospheres and space velocities of between 0.1 and 10 weight hourly space velocity (WHSV).

The ZSM-22 zeolites are also useful in the conversion of oxygenates (e.g., methanol) to gasoline-grade hydrocarbons or to chemicals, e.g., olefins. The conversion process can be conducted in a fixed bed, in a fixed bed tubular reactor or in a fluidized bed reactor. The prior art processes for carrying out such conversion with ZSM-5 and other zeolites are disclosed, e.g., in U.S. Pat. Nos. 3,894,106, 3,894,107, 3,904,508, 3,907,915, 3,931,349, 3,965,205 and 3,998,898, the entire contents of all of which are incorporated herein by reference. The ZSM-22 zeolite can be substituted for other ZSM-5 type zeolites used in the prior art. Accordingly, the process operating conditions and details will be identical to those of the aforementioned patents, except that the ZSM-22 zeolite is substituted in the process for the zeolites of the prior art. In the fluidized bed reactor, the reaction is carried out at a temperature of at least 500°

F., at pressure of 1 to 200 atmospheres and at 0.5 to 50 liquid hourly space velocity (LHSV).

In a fixed bed reactor, the process is conducted in two stages. The first stage comprises conversion of the oxygenates to dimethyl ether (in a DME reactor), and the second stage conversion of the first reactor effluent to the hydrocarbon products of the reaction. Both stages of the reaction are carried out in the presence of a catalyst: the first stage with a gamma-alumina catalyst (see, e.g., U.S. Pat. No. 3,931,349), and the second stage with a ZSM-5 type zeolite catalyst, or more specifically with a ZSM-22 zeolite catalyst.

The ZSM-22 zeolite can also be used in catalytic dewaxing of petroleum stocks. Prior art processes for catalytic dewaxing of such stocks over ZSM-5 and similar zeolites are disclosed, e.g., in U.S. Pat. Nos. 3,894,938, 4,222,855, 4,137,148, 3,668,113, 3,755,138 and 4,080,397, the entire contents of all of which are incorporated herein by reference. The ZSM-22 zeolite of this invention can be substituted as the catalyst in the processes of the aforementioned patents. Accordingly, the process conditions and operating details will be the same as those in the patents, except that the new ZSM-22 zeolite is substituted in the process for the catalysts of the prior art. Thus, the dewaxing is usually carried out by passing the feedstock over the ZSM-22 catalyst, in the presence or absence of added hydrogen, and the effluent of that step may optionally be subjected to other conventional refining steps, e.g., desulfurization and/or denitrogenation. The ZSM-22 zeolite used in the dewaxing process may have incorporated therein a hydrogen transfer functional component, such as nickel, palladium or platinum, in the amount of 0.05 to 5% by weight, based on the total weight of catalyst.

In gas oil dewaxing, the catalytic dewaxing step is conducted at a temperature of about 300°–1000° F., a pressure of 0–2000 psig, and at liquid hourly space velocity (LHSV) of 0.1 to 10 with a hydrogen to hydrocarbon ratio of about 0 to about 25:1.

In lube stock dewaxing, conditions for the catalytic hydrodewaxing step include a temperature of between about 500° F. and about 675° F., a pressure of between about 100 and about 3000 psig, preferably between about 200 and about 1000 psig. The liquid hourly space velocity is between about 0.1 and about 10, preferably between about 0.5 and about 4.0, and the hydrogen to feed ratio is about 400 to about 8000, preferably about 800 to 4000 standard cubic feet (scf) of hydrogen per barrel of feed.

Synthetic ZSM-22 zeolites can be used either in the organic nitrogen-containing and alkali metal-containing form, the alkali metal form and hydrogen form or another univalent or multivalent cationic form. The as-synthesized zeolite may be conveniently converted into the hydrogen, the univalent or multivalent cationic forms by base exchanging the zeolite to remove the sodium cations by such ions as hydrogen (from acids), ammonium, alkylammonium and arylammonium including $RNH_3^+$, $R_3NH^+$, $R_2NH_2^+$ and $R_4N^+$ where R is alkyl or aryl, provided that steric hindrance does not prevent the cations from entering the cage and cavity structure of the ZSM-22 type crystalline zeolite. The hydrogen form of the zeolite, useful in such hydrocarbon conversion processes as isomerization of polysubstituted alkyl aromatics and disproportionation of alkyl aromatics, is prepared, for example, by base exchanging the sodium form with, e.g., ammonium chloride or hydroxide whereby the ammonium ion is substituted for the sodium ion. The composition is then calcined at a temperature of, e.g., 1000° F. (about 540° C.) causing evolution of ammonia and retention of the hydrogen proton in the composition. Other replacing cations include cations of the metals of the Periodic Table, particularly metals other than sodium, most preferably metals of Group IIA, e.g., zinc, and Groups IIA, IVA, IB, IIB, IIIB, IVB, VIB and Group VIII of the Periodic Table, and rare earth metals and manganese.

Ion exchange of the zeolite can be accomplished conventionally, e.g., by admixing the zeolite with a solution of a cation to be introduced into the zeolite. Ion exchange with various metallic and non-metallic cations can be carried out according to the procedures described in U.S. Pat. Nos. 3,140,251, 3,140,252 and 3,140,253, the entire contents of which are incorporated herein by reference.

The ZSM-22 crystal can also be used as a catalyst in intimate combination with a hydrogenating component such as tungsten, vanadium, molybdenum, rhenium, nickel, cobalt, chromium, manganese, or a noble metal such as platinum or palladium where a hydrogenation-dehydrogenation function is desired. Such component can be exchanged into the composition, impregnated therein or physically intimately admixed therewith. Such component can be impregnated in or onto the zeolite, for example, in the case of platinum, by treating the zeolite with a solution containing a platinum metal-containing ion. Thus, suitable platinum compounds include chloro-platinic acid, platinous chloride and various compounds containing the platinum tetrammine-platinum complex. Combinations of the aforementioned metals and methods for their introduction can also be used.

Synthetic ZSM-22 zeolite, when employed either as an absorbent or as a catalyst in a hydrocarbon conversion process, should be at least partially dehydrated. This can be accomplished by heating the zeolite to a temperature in the range of about 200° C. to about 600° C. in an inert atmosphere, such as air or nitrogen for about 1 to about 48 hours. Simple dehydration of the crystal can also be performed at lower temperatures, such as room temperature, merely by placing the ZSM-22 zeolite type crystal in a vacuum, but a longer time is required to obtain a sufficient degree of dehydration.

In the case of many catalysts, it is desired to incorporate the new crystal with another material resistant to the temperatures and other conditions employed in organic conversion processes. Such materials include active and inactive materials and synthetic or naturally occurring zeolites as well as inorganic materials, such as clays, silica and/or metal oxides. The clays, silica and/or metal oxides may be either naturally occurring or in the form of gelatinous precipitates or gels including mixtures of silica and metal oxides. The use of such additional active material in conjunction with the new ZSM-22 crystal, i.e., combined therewith, tends to improve the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Such materials, e.g., clays or oxides, function as binders for the catalyst. It is desirable to provide a catalyst having good crush strength because in commercial use it is desirable to prevent the catalyst from breaking down into powder-like materials. These clay binders are normally employed for the purpose of improving the crush strength of the catalyst.

Naturally occurring clays which can be composited with the new zeolite include the montmorillonite and kaolin family, which families include the subbentonites, and the kaolins commonly known as Dixie, McNamee-Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the present crystal also include inorganic oxides, notably alumina.

In addition to the foregoing materials, the ZSM-22 zeolite can be composited with a porous matrix material such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. The relative proportions of finely divided crystalline material and inorganic oxide gel matrix vary widely, with the crystal content ranging from about 1 to about 90% by weight.

In order to more fully illustrate the nature of the invention and the manner of practicing same, the following examples are presented.

In the examples which follow, and elsewhere in the specification, whenever adsorption data are set forth for comparison of sorptive capacities for water, cyclohexane and n-hexane, they were determined as follows:

A weighed sample of the calcined zeolite was contacted with the desired pure adsorbate vapor in an adsorption chamber, evacuated to <1 mm pressure and contacted with 12 mm Hg of water vapor or 20 mm Hg of n-hexane or cyclohexane vapor, pressures less than the vapor-liquid equilibrium pressure of the respective adsorbate at room temperature. The pressure was kept constant (within about ±0.5 mm) by addition of adsorbate vapor controlled by a manostat during the adsorption period, which did not exceed about 8 hours. As adsorbate was adsorbed by the new crystal, the decrease in pressure caused the manostat to open a valve which admitted more adsorbate vapor to the chamber to restore the pressures to the aforementioned control levels. Sorption was complete when the pressure change was not sufficient to activate the manostat. The increase in weight was calculated as the adsorption capacity of the sample in g/100 g of calcined adsorbent.

EXAMPLE 1

$Al_2(SO_4)_3 \cdot 16H_2O$, the alumina source, potassium hydroxide, water and octanediamine, $H_2N-(CH_2)_8-NH_2$, the organic promoter, RN, were mixed together and transferred to a stainless steel autoclave. Silica sol -(30% $SiO_2$), the silica source, was added with stirring to the mixture in the autoclave. The reaction mixture composition, in mole ratios, was:

| | | |
|---|---|---|
| $SiO_2/Al_2O_3$ | = | 90 |
| $H_2O/SiO_2$ | = | 40 |
| $OH^-/SiO_2$ | = | 0.2 |
| $K^+/SiO_2$ | = | 0.3 |
| $RN/SiO_2$ | = | 0.3 |

The reaction mixture was maintained at 160° C. with stirring (400 rpm) for 3 days when crystallization was completed. The solids were separated from any unreacted components by filtration and then water washed, followed by drying at 110° C.

Adsorption capacities of the washed, dried and calcined product were:

| | |
|---|---|
| water | 2.98% wt |
| cyclohexane | 0.96% wt |
| n-hexane | 2.66% wt |

The product had molar $SiO_2/Al_2O_3 = 80$, and $\alpha$-value of 55.

X-ray analysis of the product revealed that the crystals have the following X-ray diffraction pattern:

TABLE IV

X-RAY DATA OF CALCINED ZSM-22 OF EXAMPLE 1

| Line | 2Theta | D(Å) | I/IMAX |
|---|---|---|---|
| 1 | 8.11 | 10.90 | 66 |
| 2 | 10.11 | 8.75 | 17 |
| 3 | 12.74 | 6.95 | 20 |
| 4 | 16.30 | 5.44 | 11 |
| 5 | 19.36 | 4.58 | 11 |
| 6 | 20.30 | 4.37 | 100 |
| 7 | 21.78 | 4.08 | 4* |
| 8 | 24.16 | 3.68 | 81 |
| 9 | 24.58 | 3.62 | 57 |
| 10 | 25.68 | 3.47 | 36 |
| 11 | 26.63 | 3.35 | 7 |
| 12 | 26.97 | 3.31 | 7 |
| 13 | 27.66 | 3.22 | 2 |
| 14 | 29.97 | 2.981 | 2 |
| 15 | 30.38 | 2.942 | 4 |
| 16 | 30.74 | 2.908 | 3 |
| 17 | 31.91 | 2.804 | 1 |
| 18 | 32.10 | 2.789 | 2 |
| 19 | 32.69 | 2.739 | 3 |
| 20 | 32.98 | 2.716 | 3 |
| 21 | 35.57 | 2.524 | 19 |
| 22 | 36.58 | 2.457 | 3 |
| 23 | 36.84 | 2.440 | 10 |
| 24 | 37.37 | 2.406 | 2 |
| 25 | 37.61 | 2.391 | 3 |
| 26 | 37.98 | 2.369 | 6 |
| 27 | 39.40 | 2.287 | 1 |
| 28 | 40.21 | 2.243 | 1 |
| 29 | 43.73 | 2.070 | 4 |
| 30 | 44.40 | 2.040 | 4 |
| 31 | 44.81 | 2.023 | 2 |
| 32 | 45.26 | 2.003 | 3 |
| 33 | 47.31 | 1.921 | 1 |
| 34 | 47.72 | 1.906 | 3 |
| 35 | 48.56 | 1.875 | 7 |
| 36 | 49.29 | 1.849 | 2 |
| 37 | 49.72 | 1.834 | 1 |
| 38 | 51.05 | 1.789 | 3 |
| 39 | 51.96 | 1.760 | 1 |
| 40 | 52.79 | 1.734 | 1 |
| 41 | 53.85 | 1.702 | 1 |
| 42 | 55.03 | 1.669 | 1 |
| 43 | 55.63 | 1.652 | 2 |
| 44 | 56.43 | 1.631 | 2 |
| 45 | 57.36 | 1.606 | 5 |
| 46 | 58.61 | 1.575 | 1 |

*Intensity enhanced by cristobalite

EXAMPLES 2-21

In order to determine optimum crystallization parameters for ZSM-22, a series of experiments was conducted using various mixture compositions. The crystallization of Examples 2 through 21 was conducted at 160° C. in a stirred (400 rpm) stainless steel autoclave with silica sol (30% $SiO_2$), as the silica source, and Al$_2$(SO$_4$)$_3$.16OH$_2$O or sodium aluminate (NaAlO$_2$) as the alumina source. The organic promoters employed were pentanediamine, hexanediamine, heptanediamine or octanediamine as identified in Table V below. Results of these experiments are summarized in Table V. The products were identified by X-ray diffraction analysis.

TABLE V

| Example | SiO$_2$/Al$_2$O$_3$ | H$_2$O/SiO$_2$ | OH$^-$/SiO$_2$ | M$^+$/SiO$_2$ | RN/SiO$_2$ | Crystallization Days | PRODUCT |
|---|---|---|---|---|---|---|---|
| 2 | ∞ | 40 | 0 | 0.6 | 0.3 | 1 | 60% ZSM-22 + 20% ZSM-48 |
| 3 | ∞ | 20 | 0 | 0.3 | 0.3 | 1 | 10% ZSM-22 + 90% ZSM-48 |
| 4 | 500 | 40 | 0.2 | 0.3 | 0.3 | 2 | 20% ZSM-22 + 40% ZSM-48 |
| 5 | 200 | 40 | 0 | 0.6 | 0.3 | 2 | 100% ZSM-22 |
| 6 | 200 | 40 | 0 | 0.6 | 0.3 | 2 | 100% ZSM-22 |
| 7 | 180 | 40 | 0.1 | 0.14 | 0.3 | 3 | 100% ZSM-22 |
| 8 | 90 | 40 | 0.2 | 0.3 | 0.3 | 2 | 100% ZSM-22 |
| 9 | 90 | 40 | 0.2 | 0.3 | 0.3 | 3 | 100% ZSM-22 |
| 10 | 90 | 40 | 0.2 | 0.3 | 0.3 | 4 | 100% ZSM-22 |
| 11 | 90 | 40 | 0.2 | 0.3 | 0.3 | 1 | 100% ZSM-22 |
| 12 | 90 | 40 | 0.2 | 0.3 | 0.6 | 2 | 100% ZSM-22 |
| 13 | 90 | 40 | 0.2 | 0.3 | 0.15 | 4 | ZSM-22 + trace cristobalite |
| 14 | 90 | 40 | 0.1 | 0.2 | 0.3 | 4 | ZSM-22 + trace cristobalite |
| 15 | 90 | 40 | 0 | 0.3 | 0.3 | 2 | 100% ZSM-22 |
| 16 | 90 | 40 | 0 | 0.3 | 0.3 | 2 | 60% ZSM-22 |
| 17 | 90 | 40 | 0 | 0.3 | 0.3 | 2 | 60% ZSM-22 |
| 18 | 90 | 40 | 0 | 0.6 | 0.3 | 3 | 60% ZSM-22 |
| 19 | 60 | 40 | 0.2 | 0.33 | 0.3 | 2 | 100% ZSM-22 |
| 20 | 60 | 40 | 0.2 | 0.33 | 0.3 | 4 | 100% ZSM-22 |
| 21 | 60 | 40 | 0.2 | 0.33 | 0.3 | 4 | 100% ZSM-22 |

M$^+$ was sodium in Examples 2–6, cesium in Example 18 and potassium in the remaining examples. RN was derived from pentanediamine in Example 16, hexanediamine in Examples 7, 10–14, 20, and 21, heptanediamine in Example 17, and octanediamine in the remaining examples.

The X-ray diffraction pattern of the as-synthesized ZSM-22 zeolites of Examples 20 and 21 is set forth below in Tables VI and VII, respectively.

The data for Tables VI, VII, and VIII was obtained in the same manner as the data of Table I. Accordingly, the abbreviations and symbols of Tables VI and VII have the same meaning as set forth above in connection with the discussion of Table I.

TABLE VI
X-RAY DATA FOR THE AS-SYNTHESIZED ZSM-22 OF EXAMPLE 20

| 2 × Theta | d | I/I$_o$ |
|---|---|---|
| 8.17 | 10.82 | 32 |
| 8.90 | 9.94 | 1* |
| 10.17 | 8.70 | 8 |
| 12.76 | 6.94 | 11 |
| 16.35 | 5.42 | 4 |
| 16.58 | 5.35 | 8 |
| 18.40 | 4.82 | 1+ |
| 19.45 | 4.56 | 11 |
| 19.80 | 4.48 | 3 |
| 20.40 | 4.35 | 100 |
| 21.85 | 4.07 | 1+ |
| 22.18 | 4.01 | 1 |
| 23.10 | 3.85 | 3* |
| 23.30 | 3.82 | 3* |
| 24.27 | 3.67 | 77 |
| 24.65 | 3.61 | 70 |
| 25.72 | 3.46 | 43 |
| 26.38 | 3.38 | 4 |
| 26.64 | 3.35 | 5 |
| 27.06 | 3.30 | 8 |
| 27.68 | 3.22 | 1 |
| 30.05 | 2.97 | 3 |
| 30.40 | 2.94 | 4 |
| 30.83 | 2.90 | 4 |
| 31.89 | 2.81 | 1 |
| 32.18 | 2.78 | 2 |
| 32.68 | 2.74 | 2 |
| 32.98 | 2.72 | 4 |
| 35.63 | 2.52 | 19 |
| 36.61 | 2.455 | 3 |
| 36.90 | 2.436 | 11 |
| 37.40 | 2.404 | 3 |
| 37.63 | 2.390 | 2 |
| 38.05 | 2.365 | 7 |
| 39.45 | 2.284 | 1 |
| 40.23 | 2.242 | 1 |
| 43.45 | 2.083 | 1 |
| 43.73 | 2.070 | 4 |
| 44.44 | 2.039 | 3 |
| 44.90 | 2.019 | 2 |
| 45.37 | 1.999 | 3 |
| 47.40 | 1.918 | 1 |
| 47.77 | 1.905 | 4 |
| 48.48 | 1.878 | 9 |
| 49.33 | 1.847 | 2 |
| 49.65 | 1.836 | 2 |

*Trace ZSM-5.
+Trace cristobalite.

TABE VII
X-RAY DATA FOR THE AS-SYNTHESIZED ZSM-22 OF EXAMPLE 21

| 2 × Theta | d | I/I$_o$ |
|---|---|---|
| 8.13 | 10.88 | 29 |
| 10.14 | 8.72 | 8 |
| 12.73 | 6.95 | 11 |
| 16.30 | 5.44 | 4 |
| 16.53 | 5.36 | 7 |
| 18.30 | 4.85 | 1+ |
| 19.35 | 4.59 | 10 |
| 19.76 | 4.49 | 3 |
| 20.31 | 4.37 | 100 |
| 21.75 | 4.09 | 1+ |
| 22.12 | 4.02 | 1 |
| 23.05 | 3.86 | 2 |
| 23.30 | 3.82 | 2 |
| 24.16 | 3.68 | 75 |
| 24.55 | 3.63 | 63 |
| 25.60 | 3.48 | 37 |
| 26.32 | 3.39 | 3 |
| 26.58 | 3.35 | 6 |
| 26.98 | 3.30 | 7 |
| 27.61 | 3.23 | 1 |
| 29.95 | 2.98 | 3 |
| 30.33 | 2.95 | 3 |
| 30.75 | 2.91 | 3 |
| 31.80 | 2.81 | 1 |
| 32.08 | 2.79 | 2 |

TABLE VII-continued

X-RAY DATA FOR THE
AS-SYNTHESIZED ZSM-22 OF EXAMPLE 21

| 2 × Theta | d | I/I₀ |
|---|---|---|
| 32.58 | 2.75 | 2 |
| 32.92 | 2.72 | 3 |
| 35.53 | 2.53 | 19 |
| 36.53 | 2.460 | 3 |
| 36.80 | 2.442 | 10 |
| 37.20 | 2.417 | 3 |
| 37.58 | 2.393 | 2 |
| 37.94 | 2.371 | 6 |
| 39.33 | 2.291 | 1 |
| 40.13 | 2.247 | 1 |
| 43.35 | 2.087 | 1 |
| 43.63 | 2.074 | 3 |
| 44.30 | 2.045 | 3 |
| 44.73 | 2.026 | 2 |
| 45.26 | 2.004 | 3 |
| 47.30 | 1.922 | 1 |
| 47.68 | 1.907 | 3 |
| 48.41 | 1.880 | 8 |
| 49.22 | 1.851 | 2 |
| 49.53 | 1.840 | 2 |

+Trace cristobalite.

EXAMPLES 22–24

A solution of 28.6 parts colloidal silica (30 wt. % SiO₂) and 29.8 parts water was prepared. An acid solution of 1 part aluminum sulfate (17.2 wt. % Al₂O₃), 2.3 parts potassium hydroxide and 52.3 parts water was also made. These two solutions were combined and mixed for 15 minutes. Five parts of 1,6-hexanediamine were added to the solution and the entire mixture was stirred. This solution was put into a stirred autoclave and heated to 320° F. This temperature was maintained for 72 hours.

The resultant zeolite was then filtered and washed on a Buchner Funnel and then dried overnight at 250° F.

This preparation was prepared three consecutive times and the analyses are as follows:

| Example | 22 | 23 | 24 |
|---|---|---|---|
| Zeolite | ZSM-22 | ZSM-22 | ZSM-22 |
| % Crystallinity | 120% | 140% | 135% |
| SiO₂/Al₂O₃ Ratio | 64 | 61 | 64 |
| Na, wt. % | 0.13 | 0.10 | 0.13 |
| K, wt. % | 0.21 | 0.21 | 0.22 |
| N, ppm | 660 | 1170 | 670 |

The x-ray diffraction pattern of the zeolite of Example 23 is set forth below in Table VIII.

TABLE VIII

X-RAY DATA FOR THE
AS-SYNTHESIZED ZSM-22 OF EXAMPLE 23

| Line | 2Theta | D(Å) | I/IMAX |
|---|---|---|---|
| 1 | 8.10 | 10.91 | 35 |
| 2 | 8.79 | 10.07 | 2* |
| 3 | 10.11 | 8.75 | 7 |
| 4 | 12.71 | 6.97 | 11 |
| 5 | 16.23 | 5.46 | 4 |
| 6 | 16.47 | 5.38 | 8 |
| 7 | 19.35 | 4.59 | 11 |
| 8 | 20.30 | 4.37 | 100 |
| 9 | 21.75 | 4.09 | 2 |
| 10 | 23.05 | 3.86 | 8* |
| 11 | 23.11 | 3.85 | 6* |
| 12 | 24.16 | 3.68 | 74 |
| 13 | 24.53 | 3.63 | 63 |
| 14 | 25.60 | 3.48 | 38 |
| 15 | 26.38 | 3.38 | 5 |
| 16 | 26.58 | 3.35 | 7 |
| 17 | 26.99 | 3.30 | 7 |
| 18 | 27.68 | 3.22 | 1 |
| 19 | 29.97 | 2.982 | 3 |
| 20 | 30.34 | 2.946 | 3 |
| 21 | 30.76 | 2.906 | 2 |
| 22 | 32.01 | 2.796 | 1 |
| 23 | 32.63 | 2.744 | 2 |
| 24 | 32.92 | 2.721 | 3 |
| 25 | 35.55 | 2.525 | 19 |
| 26 | 36.92 | 2.441 | 9 |
| 27 | 37.30 | 2.411 | 2 |
| 28 | 37.96 | 2.370 | 6 |
| 29 | 39.30 | 2.293 | 1 |
| 30 | 40.12 | 2.248 | 1 |
| 31 | 43.67 | 2.073 | 3 |
| 32 | 44.36 | 2.042 | 3 |
| 33 | 44.79 | 2.024 | 3 |
| 34 | 45.27 | 2.003 | 3 |
| 35 | 47.72 | 1.906 | 4 |
| 36 | 48.41 | 1.880 | 8 |
| 37 | 49.30 | 1.848 | 2 |
| 38 | 51.08 | 1.788 | 3 |
| 39 | 51.90 | 1.762 | 1 |
| 40 | 52.76 | 1.735 | 1 |
| 41 | 54.91 | 1.672 | 1 |
| 42 | 55.62 | 1.652 | 2 |
| 43 | 56.32 | 1.634 | 2 |
| 44 | 57.34 | 1.607 | 5 |
| 45 | 58.71 | 1.573 | 1 |

*Intensity enhanced by ZSM-5.

EXAMPLE 25

Catalyst Preparation from Zeolites of Examples 22–24

Samples of equal weight of zeolites of Examples 22–24 were combined and then mixed with alumina and water. This mixture was extruded into 1/16′ pellets and dried. The extruded material contained 65 parts ZSM-22 per 35 parts alumina.

The dried extrudate was calcined for three hours at 538° C. in flowing nitrogen. After cooling, the extrudate was twice contacted with an ammonium nitrate exchange solution (about 0.08 lb. NH₄NO₃/lb of extrudate) for one hour at room temperature.

The extrudate was then dried and calcined in air at 538° C. for six hours. The product analysis is as follows:

| Na, wt. % | 0.03 |
|---|---|
| N, ppm | 17 |

α (activity at 1000° F. relative to silica-alumina)=57

EXAMPLES 26–28

The catalyst of Example 25 was subjected to a feedstream of 50/50 by weight methanol and water at 30 psig pressure at 1 WHSV (methanol) to produce ethylene. The results and conditions of the three Examples are summarized below.

| Example | 26 | 27 | 28 |
|---|---|---|---|
| Temperature, °F. | 672 | 700 | 725 |
| Methanol Conversion, % by wt. | 47.5 | 60.2 | 68.8 |
| Ethylene Selectivity, % by wt. | 21.3 | 17.9 | 13.7 |

EXAMPLE 29

Heavy Stock Catalytic Dewaxing 17.6 grams of the catalyst of Example 25 was mixed with 88 grams of furfural raffinate in a pressure reactor. The reactants were allowed to react for 130 minutes at 500 psig. The results of the runs, for a product having boiling point (BP) of 650° F. or above, are summarized below.

| Run | Reaction Temp. °F. | Pour Point °F. | VI (Viscosity Index) |
|-----|-----|-----|-----|
| A | 600 | 40 | 99.9 |
| B | 550 | 65 | 106.8 |

The properties of the feedstock are set forth below. The objective of this example was the reduction of the amount of high molecular weight paraffins (waxes) so that the resultant hydrocarbon stock can be processed into more desireable products. As the above data indicates, the pour point of the feedstock was reduced considerably, indicating that ZSM-22 is an effective dewaxing zeolite.

| Feed of Example 29 | |
|---|---|
| Gravity, API | 29.2 |
| Pour Point, °F. | 0.8805 |
| KV @ 100° C., Centistokes | 9.260 |
| KV @ 130° C., Centistokes | 38.72 |
| Carbon Residue, wt. % (RCR*) | 0.11 |
| Sulfur, wt. % | 0.74 |
| Nitrogen, wt. % | 42 |
| Refractive Index @ 70° C. | 1.46513 |
| Aniline Point, °F. | 233 |

*Rams Carbon Residue

| Vacuum Distillation, % by Wt. | BP, °F. |
|---|---|
| — | 769 |
| 5 | 825 |
| 10 | 845 |
| 30 | 878 |
| 50 | 897 |
| 70 | 911 |
| 90 | 931 |
| 95 | 937 |

EXAMPLE 30

ZSM-22 was crystallized by reacting a silicate solution with an acid alum solution, both prepared as set forth below.

The silicate solution was prepared by adding, to 281 grams (g) of distilled water, 10.2 g of the 98.1% by weight sodium hydroxide (NaOH) solution, and 225 g of Q-brand sodium silicate (a brand name of sodium silicate comprising, in percent by weight, 28.5% $SiO_2$, 8.8% $Na_2O$, and 62.7% water).

The acid alum solution was prepared by adding, to 385 g of distilled water, 18.5 g of sulfuric acid (96.4% by weight), 46.4 g of diethylamine hydrochloride and 7.7 g of aluminum sulfate $[Al_2(SO_4)_3 \times 14H_2O]$.

The silicate solution and the acid aluminate solution were mixed separately in a Waring blender and then transferred to a Teflon-lined reactor bomb. The bomb was placed in a silicone oil bath at 300° F. (149° C.) for 3 days. After 3 days the bomb was removed from the bath and the contents transferred to a plastic jar and held for 11 days at room temperature. At the end of 11 days the reaction mixture was returned to the bomb and crystallization resumed at 300° F. After a total of 16 days at 300° F. the bomb was sampled, the sample was filtered out of solution, water washed and dried. The crystalline product was identified from its X-ray diffraction pattern, set forth below, as the new zeolite ZSM-22. Chemical analysis of the product gave the following results:

| $SiO_2$ | 97.0% wt |
|---|---|
| $Al_2O_3$ | 1.93% wt |
| Na | 0.30% wt |
| N | 0.76% wt |

Adsorption capacities of the washed, dried and calcined product were:

| water | 5.0% wt |
|---|---|
| cyclohexane | 0.6% wt |
| h-hexane | 3.7% wt |

X-ray analysis of the product, as synthesized, revealed that the crystals have the following X-ray diffraction pattern:

| Line | 2Theta | D(Å) | I/IMAX |
|---|---|---|---|
| 1 | 7.93 | 11.15 | 51* |
| 2 | 8.10 | 10.91 | 65 |
| 3 | 8.79 | 10.06 | 20* |
| 4 | 8.94 | 9.89 | 7* |
| 5 | 10.11 | 8.75 | 14 |
| 6 | 11.90 | 7.44 | 1* |
| 7 | 12.75 | 6.94 | 23 |
| 8 | 13.14 | 6.74 | 3* |
| 9 | 13.88 | 6.38 | 4* |
| 10 | 14.76 | 6.00 | 5* |
| 11 | 15.48 | 5.72 | 3* |
| 12 | 15.86 | 5.59 | 4* |
| 13 | 16.33 | 5.43 | 10 |
| 14 | 16.52 | 5.37 | 5* |
| 15 | 17.18 | 5.16 | 1* |
| 16 | 17.73 | 5.00 | 1* |
| 17 | 19.38 | 4.58 | 12* |
| 18 | 20.32 | 4.37 | 100 |
| 19 | 20.78 | 4.27 | 10* |
| 20 | 21.56 | 4.12 | 12 |
| 21 | 22.11 | 4.02 | 7* |
| 22 | 23.07 | 3.86 | 36* |
| 23 | 23.17 | 3.84 | 32* |
| 24 | 23.73 | 3.75 | 19* |
| 25 | 24.07 | 3.70 | 36* |
| 26 | 24.20 | 3.68 | 82 |
| 27 | 24.59 | 3.62 | 59 |
| 28 | 25.69 | 3.47 | 42 |
| 29 | 26.65 | 3.35 | 10 |
| 30 | 26.99 | 3.30 | 8 |
| 31 | 27.67 | 3.22 | 2 |
| 32 | 28.50 | 3.13 | 1 |
| 33 | 29.23 | 3.06 | 3 |
| 34 | 29.98 | 2.981 | 6 |
| 35 | 30.37 | 2.943 | 4 |
| 36 | 30.78 | 2.905 | 2 |
| 37 | 32.14 | 2.785 | 2 |
| 38 | 32.72 | 2.737 | 3 |
| 39 | 33.00 | 2.714 | 2 |
| 40 | 34.20 | 2.622 | 1* |
| 41 | 35.62 | 2.520 | 20 |
| 42 | 36.00 | 2.495 | 2* |
| 43 | 36.60 | 2.455 | 2 |
| 44 | 36.90 | 2.436 | 8 |
| 45 | 37.39 | 2.405 | 3 |
| 46 | 38.03 | 2.366 | 6 |
| 47 | 40.25 | 2.241 | 1 |
| 48 | 43.77 | 2.068 | 4 |
| 49 | 44.45 | 2.038 | 3 |

-continued

| Line | 2Theta | D(Å) | I/IMAX |
|---|---|---|---|
| 50 | 45.03 | 2.013 | 4 |
| 51 | 45.37 | 1.999 | 5 |
| 52 | 46.38 | 1.958 | 1 |
| 53 | 47.30 | 1.922 | 1 |
| 54 | 47.76 | 1.904 | 3 |
| 55 | 48.57 | 1.874 | 8 |
| 56 | 49.30 | 1.848 | 1 |
| 57 | 49.78 | 1.832 | 1 |
| 58 | 51.13 | 1.786 | 3 |
| 59 | 52.01 | 1.758 | 1 |
| 60 | 52.85 | 1.732 | 1 |
| 61 | 55.02 | 1.669 | 1 |
| 62 | 55.70 | 1.650 | 2 |
| 63 | 56.45 | 1.630 | 3 |
| 64 | 57.45 | 1.604 | 5 |
| 65 | 58.81 | 1.570 | 1 |

*Intensity enhanced by ZSM-5.

EXAMPLE 31

In this example the same chemical formulation, i.e., the same silicate and the alum solutions, was used as in Example 30. The reaction mixture, obtained by mixing the silicate and the aluminate solutions, was held for 3 days at 300° F. in the reactor bomb, then for 7 days at ambient temperature, then for 3 more days at 300° F., for a total of 6 days at 300° F. The crystalline product was sampled and the sample was washed and dried according to the procedure of Example 30. X-ray diffraction analysis of the sample showed that the crystals had the x-ray diffraction pattern of the Table in Example 30. The zeolite was determined to be 100% ZSM-22.

EXAMPLE 32

In this example the same chemical formulation, i.e., the same silicate and the alum solutions, was used as in Example 30. The reaction mixture, obtained by mixing the silicate and the aluminate solutions, was aged for 3 days at ambient temperature prior to crystallization in the reactor bomb at 300° F. After 7 days of crystallization at 300° F. the sample was held for two days at ambient temperature, then crystallization was resumed at 300° F. for a total of 12 days at 300° F. The crystalline product was also analyzed by X-ray diffraction and it was determined to have the same pattern as shown in the Table of Example 30. The product was determined to be 105% ZSM-22.

The following Examples 33–41 are taken from the aforementioned U.S. application Ser. No. 448,133 and demonstrate how ZSM-22 can be made with an N-ethylpyridium directing agent. In this regard, it is noted that when alkane diamines were used as the organic compounds, it was preferred to use larger alkali metal cations, e.g., potassium ($K^+$) or cesium ($Cs^+$), at the $SiO_2/Al_2O_3$ mole ratios of about 20 to about 90 to obtain ZSM-22 crystals substantially free of impurities or other crystals (see e.g., the aforementioned U.S. patent application Ser. No. 373,452, filed on Apr. 30, 1982) now abandoned. The use of the potassium cation may be disadvantageous in some applications because potassium is more difficult to remove than sodium from the synthesized zeolite by ammonium ion ($NH_4^+$) exchange. As is known in the art, the presence of alkali or alkaline earth cations in zeolites lowers catalytic activity thereof.

EXAMPLES 33–41

The crystallinization of ZSM-22 was conducted, in Examples 33–41, in a stainless steel autoclave stirred at about 400 revolutions per minute (rpm) at 160° C. N-ethylpyridinium bromide was used as an organic template in all examples. The N-ethylpyridinium bromide was manufactured by the Eastman Kodak Company and was used as-received without further purification. In all examples, except for Example 33, conducted without a source of added alumina, aluminum sulfate $Al_2(SO_4)_3 \cdot 16H_2O$, was used as the alumina source. Reaction mixture compositions for each example, reaction time and product identification are set forth in Table IX. The zeolite products were identified by X-ray powder diffraction analysis. Product compositions, determined by chemical analysis for zeolites of some examples, are set forth in Table X.

TABLE IX

| | | | | | | | | | |
|---|---|---|---|---|---|---|---|---|---|
| | | | Crystallizations with Ethylpyridinium Cation | | | | | | |
| Example | Silica Source | $SiO_2$ $Al_2O_3$ | $H_2O$ $SiO_2$ | $OH^-$ $SiO_2$ | $Na^+$ $SiO_2$ | $K^+$ $SiO_2$ | $R$ $SiO_2$ | Time on Stream (hours) | Product |
| 33 | Q-brand* | ∞ | 40 | 0.30 | 0.59 | — | 0.20 | 48 | 30% ZSM-22 + 70% ZSM-48 |
| 34 | Q-brand | 500 | 40 | 0.30 | 0.59 | — | 0.20 | 72 | 95% ZSM-22 + 5% ZSM-5 |
| 35 | Silica Sol** | 300 | 40 | 0.30 | 0.33 | — | 0.20 | 72 | 100% ZSM-22 |
| 36 | Silica Sol | 200 | 40 | 0.30 | 0.34 | — | 0.20 | 96 | 97% ZSM-22 + 3% ZSM-5 |
| 37 | Silica Sol | 90 | 20 | 0.30 | — | 0.39 | 0.20 | 48 | 100% ZSM-22 |
| 38 | Q-brand | 90 | 40 | 0.30 | 0.59 | — | 0.20 | 48 | 100% ZSM-22 |
| 39 | Silica Sol | 60 | 40 | 0.30 | — | 0.43 | 0.20 | 96 | 100% ZSM-22 |
| 40 | Silica Sol | 60 | 20 | 0.15 | 0.28 | — | 0.10 | 72 | 100% ZSM-22 |
| 41 | Q-brand | 60 | 40 | 0.30 | 0.59 | — | 0.20 | 72 | 100% ZSM-22 |

*Q-brand sodium silicate comprises about 28.5% by weight of $SiO_2$, 8.8% by weight of $Na_2O$ and 62.7% by weight of $H_2O$.
**Silica Sol comprises about 30% by weight of $SiO_2$ and about 70% by weight of $H_2O$.

TABLE X

| | | | | | | | |
|---|---|---|---|---|---|---|---|
| | | Product Composition of ZSM-22 Samples | | | | | |
| ZSM-22 Zeolite of Example | C (mole N ratio) | Formula per mole $Al_2O_3$ | | | Product Composition[a] | | |
| | | $N_2O$ : | $Na_2O$ : | $SiO_2$ | Al/uc | $Na^+$/uc | EtPYR/uc |
| 35 | 6.8 | 4.9 | 1.8 | 235 | 0.20 | 0.37 | 1.0 |
| 37 | 6.7 | 1.6 | n.a. | 88 | 0.53 | n.a. | 0.9 |
| 38 | 7.0 | 1.3 | 0.4 | 56 | 0.82 | 0.29 | 1.1 |
| 40 | 7.2 | 1.3 | 0.7 | 54 | 0.86 | 0.57 | 1.1 |
| 41 | 7.1 | 1.4 | 0.3 | 52 | 0.89 | 0.30 | 1.2 |

[a] "uc" is an abbreviation of "unit cell" which contains 24 ($SiO_2$ + $AlO_2^-$) tetrahedra.

The X-ray diffraction pattern of the as-synthesized ZSM-22 zeolites of Examples 35 and 39 is set forth below in Tables XI and XII, respectively.

The data for Tables XI and XII was obtained in the same manner as the data of Table I. Accordingly, the abbreviations and symbols of Tables XI and XII have the same meaning as set forth above in connection with the discussion of Table I.

TABLE XI

| 2 × Theta | d(Å) | I/I$_o$ |
|---|---|---|
| 4.46 | 19.79 | 2 |
| 8.17 | 10.81 | 75 |
| 8.34 | 10.59 | 1 |
| 10.15 | 8.71 | 19 |
| 12.82 | 6.90 | 27 |
| 16.39 | 5.40 | 12 |
| 16.54 | 5.36 | 9 |
| 19.41 | 4.57 | 7 |
| 20.34 | 4.36 | 100 |
| 24.20 | 3.67 | 96 |
| 24.68 | 3.60 | 95 |
| 25.82 | 3.45 | 80 |
| 26.34 | 3.38 | 3 |
| 26.72 | 3.33 | 8 |
| 27.02 | 3.30 | 6 |
| 30.01 | 2.98 | 2 |
| 30.47 | 2.93 | 5 |
| 30.76 | 2.90 | 4 |
| 32.21 | 2.78 | 3 |
| 32.87 | 2.72 | 3 |
| 33.08 | 2.70 | 3 |
| 35.60 | 2.52 | 17 |
| 36.56 | 2.46 | 2 |
| 36.60 | 2.45 | 2 |
| 36.92 | 2.43 | 10 |
| 37.48 | 2.40 | 3 |
| 38.01 | 2.36 | 8 |

TABLE XII

| 2 × Theta | d(Å) | I/I$_o$ |
|---|---|---|
| 8.13 | 10.86 | 40 |
| 10.09 | 8.76 | 10 |
| 12.78 | 6.92 | 13 |
| 16.38 | 5.41 | 8 |
| 19.35 | 4.58 | 10 |
| 20.26 | 4.38 | 100 |
| 24.11 | 3.69 | 97 |
| 24.58 | 3.62 | 65 |
| 25.75 | 3.46 | 46 |
| 26.63 | 3.34 | 7 |
| 26.90 | 3.31 | 5 |
| 30.59 | 2.92 | 4 |
| 35.49 | 2.53 | 19 |
| 36.76 | 2.44 | 9 |
| 37.41 | 2.40 | 4 |
| 37.57 | 2.39 | 4 |
| 37.80 | 2.38 | 7 |

The following Examples 42–48 are taken from the aforementioned U.S. application Ser. No. 373,453 (U.S. Pat. No. 5,248,841) and and demonstrate certain catalytic uses of ZSM-22.

EXAMPLE 42

Synthesis of ZSM-22 having product SiO$_2$/Al$_2$O$_3$ molar ratio of 74

Al$_2$(SO$_4$)$_3$.16H$_2$O, the source of alumina, potassium hydroxide, water and octanediamine, H$_2$N—(CH$_2$)$_8$—NH$_2$, the organic promoter, RN, were mixed together and transferred to a stainless steel autoclave. Silica sol (30 percent SiO$_2$, 70 percent H$_2$O), the silica source, was added with stirring to the mixture in the autoclave. The reaction mixture composition, in mole ratios, was:

| SiO$_2$/Al$_2$O$_3$ | = | 90 |
|---|---|---|
| H$_2$O/SiO$_2$ | = | 40 |
| OH$^-$/SiO$_2$ | = | 0.20 |
| K$^+$/SiO$_2$ | = | 0.30 |
| RN/SiO$_2$ | = | 0.30 |

The reaction mixture was stirred at 400 rpm and was maintained at 160° C. for four (4) days, at which time crystallization was completed. The crystalline solids were separated from any unreacted components by filtration and then water washed. X-ray diffraction analysis revealed that the product was 100 percent ZSM-22 zeolite. The crystals were then dried at 110° C.

The chemical composition, in moles, of the product was as follows:

| N$_2$O | = | 2.6 |
|---|---|---|
| K$_2$O | = | 0.51 |
| Al$_2$O$^3$ | = | 1.0 |
| SiO$_2$ | = | 74 |

The as-synthesized ZSM-22 powder was precalcined in a tube furnace in flowing nitrogen (150 ml/min) from room temperature to 550° C. at a rate of 2° C./min. When the sample reached 550° C., the nitrogen was replaced by air (also at 150 ml/min), and the sample was held at 550° C. for 24 hours at that air flow rate.

The calcined ZSM-22 powder was now NH$_4$$^+$-exchanged in 1.0N NH$_4$NO$_3$ solution with stirring at 80° C. for 6 hours. After exchange, the zeolite was filtered, washed with water, and dried at 110° C.

EXAMPLE 43

Synthesis of ZSM-22 having product SiO$_2$/Al$_2$O$_3$ molar ratio of 64

Solution A, containing 1.7 g Al$_2$(SO$_4$)$_3$.16H$_2$O, 3.9 g KOH, 0.2 g KCl, 10.4 g 1,8-octanediamine (C$_8$DN), and 87.8 g of water, was mixed with solution B, containing 48.0 g silica sol (30 percent SiO$_2$) and 50.0 g water, in a 300 ml stainless steel autoclave. In terms of mole ratios the hydrogel had the following composition:

| SiO$_2$/Al$_2$O$_3$ | = | 90 |
|---|---|---|
| H$_2$O/SiO$_2$ | = | 40 |
| OH$^-$/SiO$_2$ | = | 0.20 |
| K$^+$/SiO$_2$ | = | 0.30 |
| C$_8$DN/SiO$_2$ | = | 0.30 |

The hydrogel was reacted at 160° C. with stirring (400 rpm) at autogenous pressure for 2 days. The resultant product was filtered, washed with water, and dried at 110° C. X-ray and Scanning Electron Microscopic analysis of the product revealed 100 percent crystalline ZSM-22 with needle-like crystal morphology of 0.2–1.0 μm length.

EXAMPLE 44

Synthesis of ZSM-22 having product SiO$_2$/Al$_2$O$_3$ ratio of 52

Al$_2$(SO$_4$)$_3$.16H$_2$O, potassium hydroxide, water and hexanediamine, H$_2$N-(CH$_2$)$_6$-NH$_2$, were mixed together and transferred to a stainless steel autoclave. Silica sol (30 percent SiO$_2$, 70 percent H$_2$O) was added with stirring to the mixture in the autoclave. The reaction mixture composition, in mole ratios, was:

| | | |
|---|---|---|
| $SiO_2/Al_2O_3$ | = | 60 |
| $H_2O/SiO_2$ | = | 40 |
| $OH^-/SiO_2$ | = | 0.20 |
| $K^+/SiO_2$ | = | 0.33 |
| $RN/SiO_2$ | = | 0.30 |

The reaction mixture was stirred at 400 rpm and it was maintained at 160° C. for 4 days, at which time the crystallization was completed. The crystalline solids were separated from any unreacted components by filtration, and then water washed. X-ray diffraction analysis revealed that the product was 100 percent ZSM-22 zeolite.

The chemical composition, in moles, of the product was:

| | | |
|---|---|---|
| $N_2O$ | = | 2.28 |
| $K_2O$ | = | 0.45 |
| $Al_2O_3$ | = | 1.0 |
| $SiO_2$ | = | 52 |

The product was thoroughly calcined by heating at 550° C. for 15 hours.

EXAMPLE 45

Disproportionation reaction with ammonia-exchanged ZSM-22 (HZSM-22)

Three grams of ZSM-22 of Examples 42 or 44 (product $SiO_2:Al_2O_3$ mole ratio=64 or 52 respectively) were placed in a small quartz continuous-flow reactor and heated to the temperature set forth below for different runs. The pressure in the reactor was maintained at 1.0 atmosphere and the liquid hourly space velocity was as noted below. The results are summarized in Table XIII.

EXAMPLE 46

Toluene Alkylation With Methanol

Alkylation of toluene with methanol was carried out by passing a toluene/methanol mixture at 1 atmosphere, and in a molar ratio, at the temperature and LHSV conditions indicated in Table XIV below for individual runs. The results are also summarized below. The equilibrium distribution of the ortho-(O), meta-(M) and para-(P) xylene isomers for this reaction is: O=26; P=23; M=51.

TABLE XIV

| Run | ZSM-22 of Example | Toluene to Methanol Ratio (Moles) | Temperature (°C.) | LHSV | Toluene Conversion (Mole %) | Distribution of O, M, & P isomers in Xylene Products (Mole %) | | |
|---|---|---|---|---|---|---|---|---|
| | | | | | | O | M | P |
| A | 42 | 5.2 | 500 | 4.3 | 10.4 | 26 | 16 | 57 |
| B | 42 | 5.2 | 500 | 4.3 | 11.5 | 24 | 15 | 61 |
| C | 42 | 5.2 | 600 | 4.3 | 11.3 | 26 | 19 | 55 |
| D | 42 | 4.0 | 500 | 2.8 | 13.1 | 27.9 | 41.8 | 30.3 |
| E | 42 | 4.0 | 500 | 2.8 | 14.1 | 28.2 | 40.6 | 31.2 |
| F | 42 | 4.0 | 500 | 2.8 | 12.5 | 28.2 | 29.8 | 42.0 |
| G | 42 | 4.0 | 550 | 2.8 | 15.0 | 28.0 | 29.3 | 42.7 |

EXAMPLE 47

Toluene Alkylation With Ethylene

In a manner similar to that of Example 46, alkylation of toluene with ethylene was carried out by passing toluene and ethylene, at the conditions specified below for individual runs, over 3 grams of the ZSM-22 zeolite of Example 42. The results are summarized in Table XV below. The equilibrium distribution of the ortho-, meta-, and para-ethyltoluene isomers of this reaction is: O=18; P=32; M=50.

TABLE XV

| Run | Toluene to Methanol Ratio (Moles) | Temperature (°C.) | LHSV | Toluene Conversion (Mole %) | Distribution of O, M, & P isomers in Xylene Products (Mole %) | | |
|---|---|---|---|---|---|---|---|
| | | | | | O | M | P |
| A | 3.9 | 450 | 2.9 | 1.9 | — | 14 | 86 |
| B | 3.9 | 550 | 2.9 | 1.5 | — | 26 | 74 |

EXAMPLE 48

Cracking of meta-/para-cymene mixture

A mixture comprising 67 weight percent of 1-isopropyl-3-methylbenzene (meta-cymene), 28 weight percent of 1-isopropyl-4-methylbenzene (para-cymene), was

TABLE XIII

| ZSM-22 of Example | Temperature (°C.) | LHSV | Toluene Conversion (Mole %) | Distribution of Ortho (O), Meta (M) and Para (P) Isomers in Xylene Products (Mole %) | | | | | |
|---|---|---|---|---|---|---|---|---|---|
| | | | | Reaction | | | Equilibrium | | |
| | | | | O | M | P | O | M | P |
| 42 | 500 | 2.8 | 1 | 25.3 | 40.5 | 34.3 | 26 | 51.0 | 23 |
| 44 | 500 | 2.8 | 2.5 | 27.5 | 42.2 | 30.3 | | | |
| 44 | 500 | 2.8 | 2.0 | 27.2 | 41.0 | 31.8 | | | |
| 44 | 550 | 2.8 | 3.5 | 26.9 | 44.5 | 28.5 | | | |
| 44 | 550 | 2.8 | 3.5 | 26.9 | 43.9 | 29.2 | | | |
| 44 | 550 | 2.8 | 4.2 | 26.8 | 44.1 | 29.0 | | | |
| 44 | 550 | 2.8 | 3.8 | 27.6 | 42.0 | 30.3 | | | |
| 44 | 550 | 2.8 | 2.7 | 28.1 | 41.2 | 30.8 | | | | passed over 3 grams of ZSM-22 zeolite of Example 42, at the conditions summarized below in Table XVI.

TABLE XVI

| | Selective Cracking of Cymenes | | | | | |
|---|---|---|---|---|---|---|
| | Feedstock | ZSM-22 | ZSM-22 | ZSM-22 | ZSM-5 | ZSM-5 |
| Catalyst: | | | | | | |
| Temperature (°C.) | — | 300 | 300 | 400 | 250 | 250 |
| LHSV (hr$^{-1}$) of hydrocarbon | — | 1.1 | 1.1 | 1.1 | 1.1 | 2.8 |
| GHSV (hr$^{-1}$) of N$_2$ | — | 0 | 660 | 660 | 0 | 0 |
| Composition: | | | | | | |
| (Wt % of aromatics) | | | | | | |
| Benzene | 0.0 | 0.0 | | 0.38 | | |
| Toluene | 0.07 | 4.62 | 3.06 | 16.77 | | |
| Dimethylbenzene | 0.094 | 0.04 | 0.04 | 0.09 | | |
| | 0.048 | 0.08 | 0.06 | 0.08 | | |
| ortho-cymene | 4.50 | 4.54 | 4.56 | 4.02 | | |
| meta-cymene | 66.98 | 65.93 | 65.72 | 64.84 | | |
| para-cymene | 27.85 | 23.73 | 25.37 | 12.32 | | |
| n-propyltoluene | 0.278 | 0.406 | 0.388 | 0.47 | | |
| other C$_{11}$+ aromatics | 0.02 | 0.120 | 0.0 | 0.33 | | |
| % ortho in cymenes | 4.50 | 4.47 | 4.77 | 3.75 | | |
| % meta in cymenes | 67.08 | 64.90 | 68.71 | 60.47 | | |
| % para in cymenes | 27.88 | 23.36 | 26.52 | 11.49 | | |
| % Conversion of: | | | | | | |
| ortho-cymene | — | 0.7 | 14.6 | 16.7 | 2.0 | 0.2 |
| meta-cymene | — | 3.2 | 7.5 | 9.8 | 10.4 | 1.7 |
| para-cymene | — | 16.2 | 57.7 | 58.8 | 62.3 | 14.6 |

The following Examples 49 and 50 are taken from the aforementioned U.S. application Ser. No. 652,164 (U.S. Pat. No. 5,254,770) and demonstrate certain further catalytic uses of ZSM-22.

EXAMPLE A

Catalyst Preparation

Solution A, containing 192.0 g. of silica sol (30% SiO$_2$) and 200.0 g. water, was mixed with stirring with Solution B, containing 6.7 g. Al$_2$(SO$_4$)$_3$. 16H$_2$O, 15.5 g. KOH, 33.4 g. 1,6-hexanediamine (C$_6$DN), and 351.2 g. water, directly into a one-liter stainless steel autoclave. The composition of reaction mixture, in mole ratios, was: SiO$_2$/Al$_2$O$_3$=90; H$_2$O/SiO$_2$=40; OH$^-$/SiO$_2$=0.20; K$^+$/SiO$_2$=0.29; C$_6$DN/SiO$_2$=0.30.

The thus formed hydrogel was heated at 160° C. with stirring (400 rpm) for 2 days at autogenous pressure. The resultant crystalline product was filtered, washed with water, and dried on a filter funnel at 110° C. X-ray and scanning electron microscopy (SEM) analysis of the product crystals revealed 100% crystalline ZSM-22 with needle-like crystal morphology (0.5-1.0 μm in length). The crystals had SiO$_2$/Al$_2$O$_3$ mole ratio of 76 as determined by chemical analysis.

A portion of the sample of the zeolite was heated in a tube furnace in flowing nitrogen (150 ml/ml) at a rate of 2° C./min to 550° C., whereupon the flowing gas was switched to air. The sample was heated in air at 550° C. for 24 hours, then cooled to room temperature.

The calcined zeolite was now placed in a cannister and ballmilled for 17 hours. This ballmilling procedure was capable of fracturing the needle-like ZSM-22 crystals to smaller, roughly equidimensional crystals, without loss of x-ray crystallinity.

The ballmilled crystals were now NH$_4$$^+$-exchanged in one molar (1M) NH$_4$NO$_3$ solution twice at 80° C., with stirring, for a total of 6 hours, filtered, washed with water, then dried.

The material was then mixed with alumina monohydrate in a 65% zeolite, 35% alumina preparation and extruded to produce 1/16 inch cylindrical particles.

EXAMPLE B

Catalyst Preparation

Solution A, containing 192.0 g. silica sol (30% SiO$_2$) and 200.0 g. water, was mixed with stirring with Solution B, containing 3.4 g. Al$_2$(SO$_4$)$_3$. 16H$_2$O, 5.5 g. NaOH, 33.4 g. 1,6-hexanediamine (C$_6$DN), and 354.1 g. water, directly into a one-liter stainless steel autoclave. The composition of this mixture, in mole ratios, was:

SiO$_2$/Al$_2$O$_3$=180; H$_2$O/SiO$_2$=40; OH$^-$/SiO$_2$=0.10;

Na$^+$/SiO$_2$=0.14; C$_6$DN/SiO$_2$=0.30.

The hydrogel was heated at 160° C., with stirring at 400 rpm, at autogenous pressure for 3 days. The crystalline product was filtered, washed with water, and dried. X-ray and SEM analysis of the product showed 100% crystalline ZSM-22 crystals with needle-like morphology (1.0 μm in length). The SiO$_2$/Al$_2$O$_3$ mole ratio of the product was 156.

5.2 g. of this product was heated for 10 hours in flowing dry N$_2$ gas. when cooled to 25° C., it was saturated with NH$_3$ gas, followed by ion exchanges for 4, 16 and 4 hours, respectively, with 260 ml. of 2N NH$_4$NO$_3$. It was then washed at reflux with 260 ml. of water, followed by an air calcination for 10 hours at 600° C. Finally, 0.75 g. of this material, sized to 14–30 mesh, was impregnated with 2 ml. of aqueous solution containing 0.011% of Pt(NH$_3$)$_4$Cl$_2$. This final product contained 0.013% Pt on HZSM-22.

EXAMPLE 49

Isomerization Process

A synthetic C$_8$ aromatic feed was passed over the catalyst of Example A at 200 psig, hydrogen:hydrocarbon mole ratio (H$_2$/HC) of 4, and temperatures and weight hourly space velocity (WHSV) of between 850° and 900° F., and 5 and 20, respectively. The experimental conditions, and feed and product analyses are given in Table XVII. As can be seen, at 900° F. and WHSV=5, near equilibrium p-xylene concentrations are achieved (93% of equilibrium) and xylene selectivity is very good (xylene loss is less than 1.3%).

EXAMPLE 50

Isomerization Process

A synthetic $C_8$ aromatic feed was passed over the catalyst of Example B at temperatures between 900° and 1052° F. and WHSV between 5 and 20 and at 200 psig and $H_2/HC=4$. The experimental conditions and feed and product analyses are summarized in Table XVIII. At 900° F. and WHSV=5 (Samples 1, 4 and 10), high isomerization activity is demonstrated by near equilibrium (92% of equilibrium) concentrations of p-xylene and the xylene selectivity is very good (xylene losses are less than 0.35%).

TABLE XVII

| Sample | Feed | 1 | 2 | 3 | 4 | 5 | 6 | 7 |
|---|---|---|---|---|---|---|---|---|
| Time On Stream | | | | | | | | |
| (hrs) | | 16.23 | 28.13 | 29.63 | 32.97 | 34.63 | 36.14 | 39.49 |
| (days) | | 0.68 | 1.17 | 1.23 | 1.37 | 1.44 | 1.51 | 1.64 |
| Temperature (°F.) | | 901 | 899 | 899 | 850 | 851 | 851 | 902 |
| Pressure (psig) | | 200 | 200 | 200 | 200 | 200 | 200 | 200 |
| $H_2/HC$ (psig) | | 4 | 4 | 4 | 4 | 4 | 4 | 4 |
| WHSV | | 5 | 10 | 20 | 5 | 10 | 20 | 5 |
| Liquid Product Analyses (Wt. %) | | | | | | | | |
| Light gas | | 1.33 | 0.55 | 0.31 | 0.00 | 0.26 | 0.17 | 0.95 |
| Benzene | | 3.16 | 1.59 | 0.86 | 1.64 | 0.85 | 0.45 | 2.86 |
| Toluene | 0.10 | 1.00 | 0.43 | 0.25 | 0.48 | 0.28 | 0.19 | 0.80 |
| n-$C_9$ | | | | | | | | |
| ethylbenzene (EB) | 19.73 | 14.63 | 16.99 | 17.36 | 16.76 | 17.90 | 18.58 | 15.09 |
| p-xylene[a] | 9.46 | 18.26 | 16.80 | 14.28 | 17.93 | 15.64 | 13.36 | 17.99 |
| | 11.8 | 23.2 | 21.1 | 17.6 | 22.33 | 19.49 | 16.63 | 22.71 |
| m-xylene[a] | 50.57 | 41.72 | 44.89 | 47.05 | 43.93 | 46.17 | 48.19 | 42.49 |
| | 63.1 | 53.1 | 56.3 | 58.2 | 54.71 | 57.53 | 59.98 | 53.64 |
| o-xylene[a] | 20.10 | 18.64 | 18.09 | 19.58 | 18.43 | 18.44 | 18.80 | 18.73 |
| | 25.1 | 23.7 | 22.7 | 24.2 | 22.95 | 22.98 | 23.40 | 23.65 |
| Ethyl toluene (ETol) | | 0.26 | 0.11 | 0.04 | 0.03 | 0.03 | 0.03 | 0.10 |
| Trimethyl benzene (TMB) | | 0.28 | 0.12 | 0.05 | 0.19 | 0.08 | 0.01 | 0.24 |
| para-diethyl benzene (p-DEB) | 0.40 | 0.25 | 0.14 | 0.37 | 0.20 | 0.10 | 0.40 | |
| m,o-DEB | | 0.03 | 0.01 | 0.01 | 0.02 | 0.01 | 0.00 | 0.03 |
| dimethyl ethyl benzene (DMEB) | 0.31 | 0.12 | 0.03 | 0.04 | 0.04 | 0.01 | 0.27 | |
| Other $C_9^+$ (total) | | 1.28 | 0.61 | 0.27 | 0.65 | 0.36 | 0.15 | 1.04 |
| Total xylenes | 80.13 | 78.62 | 79.78 | 80.90 | 80.29 | 80.25 | 80.35 | 79.21 |
| p-xylene (% of Equilibrium) | 49.2 | 96.8 | 87.7 | 73.5 | 93.0 | 81.20 | 69.3 | 94.6 |
| Benzene/EB Conv. | | 0.83 | 0.77 | 0.48 | 0.74 | 0.62 | 0.52 | 0.82 |
| EB/EB (%) | | 25.8 | 13.9 | 12.0 | 15.05 | 9.28 | 5.83 | 23.5 |
| Xyl/Xyl (%) | | 1.22 | 0.51 | 0.19 | 0.40 | 0.20 | 0.05 | 0.73 |
| Ratio | | 21.2 | 27.4 | 63.1 | 37.6 | 46.4 | 116. | 32.2 |

[a]Numbers appearing immediately below this line are percentages of the indicated xylenes in the total xylene product.

TABLE XVIII

| Sample | Feed | 1 | 2 | 3 | 4 | 5 | 6 | 7 | 8 | 9 | 10 |
|---|---|---|---|---|---|---|---|---|---|---|---|
| Time On Stream | | | | | | | | | | | |
| (hrs) | | 4.21 | 6.58 | 8.12 | 21.49 | 25.88 | 29.87 | 31.41 | 33.03 | 35.11 | 51.24 |
| (days) | | 0.18 | 0.27 | 0.34 | 0.90 | 1.08 | 1.24 | 1.31 | 1.38 | 1.46 | 2.14 |
| Temperature (°F.) | | 900 | 901 | 902 | 900 | 904 | 900 | 950 | 1000 | 1052 | 902 |
| Pressure (psig) | | 200 | 200 | 200 | 200 | 200 | 200 | 200 | 200 | 200 | 200 |
| $H_2/HC$ (psig) | | 4 | 4 | 4 | 4 | 4 | 4 | 4 | 4 | 4 | 4 |
| WHSV | | 5 | 10 | 20 | 5 | 7.5 | 20 | 20 | 20 | 20 | |
| Liquid Product Analyses (Wt. %) | | | | | | | | | | | |
| Light gas | | 3.65 | 1.27 | 0.60 | 4.56 | 1.67 | 0.77 | 0.93 | 1.35 | 1.80 | 1.99 |
| Benzene | | 4.17 | 2.16 | 1.22 | 5.30 | 2.93 | 1.26 | 2.07 | 3.28 | 4.67 | 4.13 |
| Toluene | 0.10 | 1.34 | 0.67 | 0.35 | 1.37 | 0.75 | 0.29 | 0.54 | 0.98 | 1.76 | 0.94 |
| n-$C_9$ | | | | | | | | | | | |
| ethylbenzene (EB) | 19.73 | 12.50 | 15.93 | 17.28 | 12.51 | 14.86 | 17.42 | 16.42 | 14.66 | 12.53 | 13.69 |
| p-xylene[a] | 9.46 | 17.21 | 16.46 | 14.37 | 17.04 | 16.86 | 14.01 | 15.02 | 16.04 | 16.43 | 17.44 |
| | 11.8 | 22.2 | 20.7 | 17.9 | 22.6 | 21.30 | 17.5 | 18.9 | 20.2 | 20.9 | 22.2 |
| m-xylene[a] | 50.57 | 43.77 | 42.50 | 48.04 | 42.51 | 45.53 | 47.10 | 46.59 | 45.18 | 44.01 | 44.17 |
| | 63.1 | 56.5 | 56.9 | 59.9 | 56.3 | 57.5 | 58.9 | 58.5 | 57.0 | 56.0 | 56.2 |
| o-xylene[a] | 20.10 | 16.48 | 17.74 | 17.81 | 15.95 | 16.78 | 18.84 | 18.02 | 18.05 | 18.15 | 17.03 |
| | 25.1 | 21.3 | 22.3 | 22.2 | 21.1 | 21.2 | 23.6 | 22.6 | 22.8 | 23.1 | 21.7 |
| Ethyl toluene (ETol) | | 0.22 | 0.15 | 0.06 | 0.16 | 0.16 | 0.05 | 0.08 | 0.13 | 0.18 | 0.17 |
| Trimethyl benzene (TMB) | | 0.04 | 0.01 | 0.05 | 0.03 | 0.02 | 0.02 | 0.07 | 0.06 | 0.08 | 0.02 |
| para-diethyl benzene (p-DEB) | | 0.21 | 0.15 | 0.11 | 0.18 | 0.13 | 0.04 | 0.07 | 0.11 | 0.17 | 0.16 |
| m,o-DEB | | 0.19 | 0.03 | 0.00 | 0.14 | 0.15 | 0.14 | 0.18 | 0.09 | 0.08 | 0.16 |
| dimethyl ethyl benzene (DMEB) | | 0.04 | 0.02 | 0.00 | 0.00 | 0.05 | 0.01 | 0.03 | 0.03 | 0.05 | 0.02 |
| Other $C_9^+$ (total) | | 0.70 | 0.36 | 0.22 | 0.51 | 0.51 | 0.26 | 0.33 | 0.42 | 0.56 | 0.53 |
| Total xylenes | | 77.46 | 79.40 | 80.22 | 75.50 | 79.17 | 79.95 | 79.63 | 79.27 | 78.59 | 78.64 |
| p-xylene (% of Equilibrium) | | 92.6 | 86.4 | 74.6 | 94.0 | 88.7 | 73.0 | 78.6 | 84.3 | 87.1 | 92.4 |
| Benzene/EB Conv. | | 0.77 | 0.76 | 0.66 | 0.84 | 0.80 | 0.73 | 0.83 | 0.86 | 0.86 | 0.91 |
| EB/EB (%) | | 36.6 | 19.3 | 12.42 | 36.6 | 24.70 | 11.71 | 16.78 | 25.70 | 36.49 | 30.61 |
| Xyl/Xyl (%) | | 0.30 | 0.17 | 0.14 | 0.20 | 0.22 | 0.09 | 0.22 | 0.25 | 0.34 | 0.20 |

TABLE XVIII-continued

| Sample | Feed | 1 | 2 | 3 | 4 | 5 | 6 | 7 | 8 | 9 | 10 |
|---|---|---|---|---|---|---|---|---|---|---|---|
| Ratio | | 122.0 | 113.5 | 87.3 | 187.2 | 112.3 | 130.1 | 76.3 | 102.8 | 107.3 | 153.0 |

*Numbers appearing immediately below this line are percentages of the indicated xylenes in the total xylene product.

It will be apparent to those skilled in the art that the specific embodiments discussed above can be successfully repeated with ingredients equivalent to those generically or specifically set forth above and under variable process conditions.

From the foregoing specification one skilled in the art can readily ascertain the essential features of this invention and without departing from the spirit and scope thereof can adopt it to various diverse applications.

What is claimed is:

1. A siliceous porous crystalline ZSM-22 zeolite material having a composition, expressed in terms of moles of anhydrous oxides, as follows comprising:

$$(y)M_{2/n}O: (z)L_2O_3: 100SiO_2$$

wherein M is an alkali or alkaline earth metal having a valence n, y=0 to 2.0, z=0 to 5, and L is aluminum (Al), and having an X-ray diffraction pattern of Table I.

2. A zeolite material of claim 1, prepared from a reaction mixture comprising diethylamine hydrochloride.

3. A zeolite material of claim 2, having a calculated composition, in as-synthesized form, in terms of moles of oxides, after dehydration, per 100 moles of silica, as follows:

$$(x)Q_2O:(y)M_{2/n}O:(z)L_2O_3:100SiO_2$$

wherein $Q_2O$ is the oxide form of said diethylamine hydrochloride, M is an alkali metal or alkaline earth metal having a valence n, x=0.01–2.0, y=0–2.0, z=0–5, and L=Al.

4. A zeolite material of claim 1 prepared from a reaction mixture comprising octanediamine and potassium ions.

5. A zeolite material of claim 1 prepared from a reaction mixture comprising hexanediamine and potassium ions.

6. A zeolite material obtained by ion exchanging alkali or alkaline earth metal from the ZSM-22 material of claim 60.

7. A zeolite material of claim 6, wherein the alkali or alkaline earth metal is exchanged with ammonium.

8. A zeolite material of claim 7, wherein, following the exchange, the composition is calcined at about 1000° F.

9. A zeolite material of claim 4 having a calculated composition, in as-synthesized form, in terms of moles of oxides, after dehydration, per 100 moles of silica, as follows:

$$(0.02\ to\ 10)RN:(0\ to\ 2)K_2O:(0\ to\ 5)Al_2O_3:100SiO_2$$

wherein RN is said octanediamine.

10. A zeolite material of claim 5 having a calculated composition, in as-synthesized form, in terms of moles of oxides, after dehydration, per 100 moles of silica, as follows:

$$(0.02\ to\ 10)RN:(0\ to\ 2)K_2O:(0\ to\ 5)Al_2O_3:100SiO_2$$

wherein RN is said hexanediamine.

11. A siliceous porous crystalline ZSM-22 zeolite material having a framework composition, expressed in terms of moles of oxides, as follows:

$$(z)Al_2O_3:100SiO_2$$

wherein z=0 to 5, and having an X-ray diffraction pattern of Table I.

12. A zeolite material of claim 11 having a calculated composition, in as-synthesized form, in terms of moles of oxides, after dehydration, per 100 moles of silica, as follows:

$$(x)Q_2O:(y)M_{2/n}O:(z)L_2O_3:100SiO_2$$

wherein $Q_2O$ is the oxide form of an organic compound containing an element of Group 5-B of the Periodic Table, said organic compound containing at least one alkyl or aryl group having at least 2 carbon atoms, M is an alkali metal or alkaline earth metal having a valence n, x=0.01 to 2.0, y=0 to 2.0, z=0 to 5, and L=Al.

* * * * *

UNITED STATES PATENT AND TRADEMARK OFFICE
CERTIFICATE OF CORRECTION

PATENT NO. : 5,336,478
DATED : August 9, 1994
INVENTOR(S) : F.G. Dwyer et al.

It is certified that error appears in the above-identified patent and that said Letters Patent is hereby corrected as shown below:

Col. 29, claim 1, line 20, after "oxides" delete "as follows"

Signed and Sealed this

Eighth Day of November, 1994

Attest:

BRUCE LEHMAN

*Attesting Officer*     *Commissioner of Patents and Trademarks*